ized Patent [19]

Morikawa et al.

[11] 4,071,575
[45] Jan. 31, 1978

[54] PROCESS FOR PRODUCING 2,6-DIMETHYL-1,3,6-OCTATRIENE

[75] Inventors: Hiroyuki Morikawa; Shoji Kitazume, both of Amimachi, Japan

[73] Assignee: Mitsubishi Petrochemical Company Limited, Japan

[21] Appl. No.: 737,069

[22] Filed: Nov. 1, 1976

[30] Foreign Application Priority Data

Nov. 11, 1975   Japan .................. 50-135541

[51] Int. Cl.² ................................. C07C 3/18
[52] U.S. Cl. ....................... 260/677 R; 260/680 B
[58] Field of Search ................... 260/677 R, 680 B

[56] References Cited

U.S. PATENT DOCUMENTS 3,932,550   1/1976   Morikawa et al. .............. 260/677 R Primary Examiner—C. Davis
Attorney, Agent, or Firm—Robert E. Burns; Emmanuel J. Lobato; Bruce L. Adams

[57] ABSTRACT

A process for producing 2,6-dimethyl-1,3,6-octatriene from the catalytic dimerization over a catalyst comprising the following components I, II and III:

I. A zirconium compound having the following formula or a complex of the zirconium compound and coordinating compound:

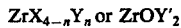

wherein X represents a halogen atom; Y and Y' respectively represent an alkoxy or chloroalkoxy group having from 1 to 20 carbon atoms, an aryloxy or chloroaryloxy group wherein the aryloxy group is a phenoxy or methyl-substituted phenoxy group, or an acyloxy group having the formula RCOO— wherein R is an alkyl group having from 1 to 20 carbon atoms or an aryl group; and n is an integer of 1 to 4;

II. An iodine compound having the formula:

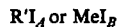

wherein R' represents hydrogen, a halogen atom, a straight or branched chain hydrocarbon group having from 1 to 20 carbon atoms or a cyclic hydrocarbon group having from 3 to 10 carbon atoms; A is an integer of 1 to 3; Me represents a metal of Groups I through IV of the periodic table; and B represents a valence of said metal; and III. An organoaluminum compound having the formula:

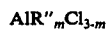

wherein R" represents an alkyl group having from 1 to 10 carbon atoms, a cycloalkyl group having from 3 to 10 carbon atoms, or an aryl group, and m is 1.5 or 2; wherein when iodine is present as a ligand in the zirconium compound I, the iodine compound II may be excluded.

12 Claims, No Drawings

PROCESS FOR PRODUCING 2,6-DIMETHYL-1,3,6-OCTATRIENE

BACKGROUND OF THE INVENTION

The present invention relates to a process for producing a chain or acyclic dimer of isoprene from the catalytic dimerization thereof.

More specifically, the present invention relates to a process for the catalytic production of 2,6-dimethyl-1,3,6-octatriene (hereinafter referred to as DMOT in some cases) wherein the catalyst used is unique.

Heretofore, as a catalyst for use in the production of the chain dimer of isoprene, DMOT, from the catalytic dimerization of isoprene, various types of Ziegler catalysts are known. Among these, a catalyst comprising a specific zirconium compound as one catalytic component has been proposed as a catalyst having a high selectivity of chain dimer formation.

Ordinarily, the catalytic dimerization reaction of isoprene is carried out in a solution. When this reaction is to be carried out on an industrial scale, a desirable embodiment is one which uses a larger proportion of isoprene feed with a smaller proportion of a solvent in order to improve productivity per reaction vessel.

However, the conventional zirconium-based catalysts have required a high concentration of catalyst and a high reaction temperature in order to increase the conversion of isoprene. This requirement of a high concentration of catalyst causes not only deterioration of the unit consumption of the catalyst (the zirconium-based catalysts being expensive), but also complication of the post treatment process after the reaction has been completed. That is, when the catalyst after the reaction completion is decomposed to remove it, the formation of an emulsion is accelerated, which makes it difficult to remove the catalyst. Furthermore, when the reaction is carried out at a high concentration of catalyst and a high reaction temperature, the conventional catalyst systems often produce sticky polymer byproducts in the course of the reaction which stain the reaction vessel, rendering the continuation of the reaction infeasible. Accordingly, the development of a catalyst having a high activity at lower concentrations of the catalyst and lower reaction temperatures has been an important problem yet to be solved. As one approach to this problem, we have previously proposed a zirconium-based catalyst modified with an electron donor containing phosphorus, as disclosed in Japanese Patent Publication NO. 7565/75, and a catalyst system containing a zirconium compound having a special ligand, as disclosed in Japanese Patent Laid-Open Publication No. 50305/75.

In addition, we have made attempts to improve a titanium-based catalyst which is more catalytically active and less expensive than the zirconium-based catalysts but has a poor selectivity of chain formation and, as a result, have proposed a titanium-based catalyst modified with an iodine compound, as disclosed in Japanese Patent Application NO. 98872/74. With these types of catalyst systems which use an iodine compound as one of their features, the selectivity of chain dimer formation has been highly improved while maintaining the high activity characteristic of the titanium-based catalysts. Accordingly, the function and effect of the iodine compound can be said to be remarkably unique.

However, these catalysts are still not fully satisfactory in that the formation of cyclic dimer byproducts, the boiling point of which is close to that of the chain dimer, cannot be fully suppressed. As a result, the production of a chain dimer with high purity requires a relatively complex separation and purification process.

SUMMARY OF THE INVENTION

It is an object of the present invention to improve the conventional zirconium-based catalysts and to further improve the above mentioned zirconium-based catalysts we have previously developed in order to enhance the catalytic activity and the selectivity of chain dimer formation, thereby realizing a chain dimerization of isoprene with a lower concentration of catalyst and a lower reaction temperature. We have found that the above object can be achieved by modifying the zirconium-based catalysts with iodine compounds as described hereinafter. In accordance with the present invention, there is provided a process for producing 2,6-dimethyl-1,3,6-octatriene which comprises contacting isoprene with a dimerization catalyst thereby to dimerize the isoprene, said dimerization catalyst comprising a combination of:

I. a zirconium compound selected from the group consisting of:
1. compounds having the general formula $$ZrX_{4-n}Y_n,$$

2. compounds having the general formula $$ZrOY'_2, \text{ and}$$

3. complexes of the compound (1) or (2) with a coordinating compound, wherein X represents a halogen atom; Y and Y' respectively represent a member selected from the group consisting of (i) alkoxy and chloroalkoxy groups each having from 1 to 20 carbon atoms, (ii) aryloxy and chloroaryloxy groups wherein each aryloxy group is a member selected from the group consisting of phenoxy and methyl-substituted phenoxy groups, and (iii) acyloxy groups each having the general formula RCOO— wherein R is a member selected from the group consisting of alkyl groups each having from 1 to 20 carbon atoms and aryl groups each having from 6 to 20 carbon atoms; and n is an integer of 1 to 4:

II. an iodine compound which is a member selected from the group consisting of those having either of the general formulas $$R'I_A \text{ and } MeI_B$$

wherein R' represents a member selected from the group consisting of hydrogen, halogen atoms, straight and branched chain hydrocarbon groups each having from 1 to 20 carbon atoms and cyclic hydrocarbon groups each having from 3 to 10 carbon atoms; A is an integer of 1 to 3; Me represents a metal of Groups I through IV of the periodic table; and B represents the valence of the metal; and III. an organoaluminum compound having the general formula $$AlR''_m Cl_{3-m}$$

wherein R" represents a member selected from the group consisting of alkyl groups each having from 1 to 10 carbon atoms, cyclic alkyl groups each having from 3 to 10 carbon atoms, and aryl groups each having 6 to 10 carbon atoms; and $m$ is 1.5 or 2; in which dimenzation catalyst, when iodine is present as a ligand in the zirconium compound I, the iodine compound II may be excluded.

The catalyst of the present invention has a catalytic activity which is several times higher than those of the conventional zirconium-based catalysts and the above mentioned improved zirconium-based catalysts we have previously proposed. As a result, even if the catalyst is used in a very small quantity with respect to isoprene, e.g., at a molar ratio of zirconium compound to isoprene of 0.0001 to 0.001, the reaction velocity is high to a satisfactory degree. Because the molar ratio of zirconium compound to isoprene has been in the range of the order of 0.002 to 0.02 for the conventional zirconium-based catalyst (as mentioned in Japanese Patent Laid Open Publication NO. 5706/73), it can be stated that the activity of the catalyst of the present invention is remarkably high.

Because of its high activity, the catalyst of the present invention makes possible the practice of the isoprene dimerization reaction at a lower temperature, which results in reduction in the production of the byproducts. Further, when the present catalyst is used, no formation of sticky polymers is observed (this being attributable in part to the high effectiveness of the catalyst in regulating the dimerization), and the load on the catalyst separation and removal process is reduced. Moreover, the reaction solution is prevented from being converted into a emulsion during this process. If the sticky products are once formed, it will be necessary to shut down the operation to clean the reaction vessel. In accordance with the present invention, there is little or no necessity for such an operation. As a result, a prolonged operation or continuous operation can be easily carried out according to the present invention.

Such a high activity of the catalyst of the present invention could not be anticipated. This is because it is believed that the iodine compound functions to improve the selectivity of chain dimer formation rather than the catalytic activity for the above mentioned titanium-based catalyst we have previously proposed. Furthermore, in the above mentioned prior catalyst, the use of the coordinating compound or electron donor compound was considered to be indispensable, and improved results were being realized, whereas the catalyst of the present invention does not require such a compound.

DETAILED DESCRIPTION

1. Catalyst

The catalyst of the present invention comprises a combination of a zirconium compound, an iodine compound, and an organoaluminum compound.

1. Zirconium compound

A zirconium compound suitable for use in the present invention is represented by the formula:

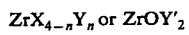

wherein X represents a halogen atom such as chlorine, bromine or iodine, particularly chlorine: Y and Y' respectively represent an alkoxy or chloroalkoxy group having from 1 to 20 carbon atoms, preferably from 1 to 12 carbon atoms, such as methoxy, ethoxy, propoxy, butoxy, octoxy, decoxy, dodecoxy, octadecoxy, or monochloro- or polychloro-derivatives thereof, particularly monochloro-derivatives; an aryloxy or chloroaryloxy group wherein the aryloxy group is a phenoxy or methyl-substituted phenoxy group, for example, phenoxy, tolyloxy, xyloxy or monochloro- and polychloro-derivatives thereof, particularly monochloro-derivatives thereof; or an acyloxy having the formula RCOO— wherein R represents an alkyl group having from 1 to 20 carbon atoms, particularly from 1 to 12 carbon atoms, or an aryl group having from 6 to 20 carbon atoms, particularly phenyl or methyl-substituted phenyl groups, for example, acetoxy, butanoyloxy, octanoyloxy or naphthenoyloxy ($C_xH_{2x-1}COO—$, $X = 8 - 10$); and $n$ is an integer of 1 to 4.

These zirconium compounds may be used in the form of a more stable zirconium complex wherein the zirconium compounds are coordinated with a coordinating compound, that is, a compound having a non-covalent electron pair such as oxygen, nitrogen, sulfur or phosphorus. Examples of the coordinating compound suitable for the present invention are ethers such as dimethyl ether and diethyl either; primary, secondary and tertiary amines such as dimethylamine, triethylamine, ethylenediamine and triethanolamine; sulfoxides and sulphones such as dimethyl sulfoxide, dimethyl sulfone and sulfolane; phosphines such as trimethylphosphine, tributylphosphine, triphenylphosphine and tricresylphosphine. These complexes need not be preformed as a material for the preparation of the catalyst and may be formed in situ in the dimerization when the zirconium compound is mixed with the other components to prepare the catalyst. The quantity of the coordinating compound is usually stoichiometric.

Examples of the above mentioned zirconium compound are:
tetrachloroethoxyzirconium $Zr(OC_2H_4Cl)_4$,
tetrachloropropoxyzirconium $Zr(OC_3H_6Cl)_4$,
tetrachlorobutoxyzirconium $Zr(OC_4H_8Cl)_4$,
chloroethoxytrichlorozirconium $Zr(OC_2H_4Cl)Cl_3$,
chloropropoxytrichlorozirconium $Zr(OC_3H_6Cl)Cl_3$,
di(chloroethoxy)dichlorozirconium $Zr(OC_2H_4Cl)_2Cl_2$,
di(chlorobutoxy)dichlorozirconium $Zr(OC_4H_8Cl)_2Cl_2$,
di(chlorobutoxy)dibromozirconium $Zr(OC_4H_8Cl)_2Br_2$,
di(chlorododecoxy)dichlorozirconium
    $Zr(OC_{12}H_{24}Cl)_2Cl_2$,
tri(chloroethoxy) chlorozirconium $Zr(OC_2H_4Cl)_3Cl$,
tri(chloropropoxy)chlorozirconium $Zr(OC_3H_6Cl)_3Cl$,
di(butoxy)diiodozirconium $Zr(OC_4H_9)_2I_2$,
tri(ethoxy)monoiodozirconium $Zr(OC_2H_5)_3I$,
tetraethoxyzirconium $Zr(OC_2H_5)_4$,
tetraphenoxyzirconium $Zr(OC_6H_5)_4$,
tributoxychlorozirconium $Zr(OC_4H_9)_3Cl$,
dimethoxydichlorozirconium $Zr(OCH_3)_2Cl_2$,
ditolyloxydichlorozirconium $Zr(OC_6H_4CH_3)_2Cl_2$,
zirconyl dibutoxide $ZrO(OC_4H_9)_2$,
zirconyl diphenoxide $ZrO(OC_6H_5)_2$,
zirconyl dichloropropoxide $ZrO(OC_3H_6Cl)_2$,
zirconyl dichlorophenoxide $ZrO(OC_6H_4Cl)_2$
zirconium tetraacetate $Zr(OCOCH_3)_4$,
zirconium tetraoctanoate $Zr(OCOC_7H_{15})_4$,
zirconium tetranaphthenate $Zr(OCOC_nH_{2n-1})_4$ ($n=8 - 10$)
zirconium tetrastearate $Zr(OCOC_{17}H_{35})_4$,
zirconyl diacetate $ZrO(OCOCH_3)_2$,
zirconyl dioctanoate $ZrO(OCOC_7H_{15})_2$,
zirconyl dinaphthenate $ZrO(OCOC_nH_{2n-1})_2$, $n=8 - 10$
zirconyl dihexanoate $ZrO(OCOC_5H_{11})_2$, and
triphenylphosphine complex $Zr(OC_3H_6Cl)Cl_3 \cdot PPh_3$.

As the zirconium compound (2), zirconyl dioctanoate, zirconyl dinaphthenate, zirconyl dihexanoate as well as zirconyl diacetate are preferable.

2. Iodine compound

Iodine compounds which can be used in the present invention are organic iodine compounds having the formula $R'I_A$ or inorganic iodine compounds having the formula $MeI_B$. In these formulae, R represents hydrogen; a halogen atom such as chlorine, bromine and iodine, particularly chlorine; a straight or branched chain, saturated or unsaturated hydrocarbon having from 1 to 20 carbon atoms, preferably from 1 to 10 carbon atoms, or an alicyclic hydrocarbon having from 3 to 10 carbon atoms, preferably from 3 to 8 carbon atoms, or an aromatic hydrocarbon, having from 6 to 10 carbon atoms, and A is an integer of 1 to 3. Me represents a metal of Groups I through IV of the periodic table such as sodium, lithium, zinc, aluminum, titanium, tin, zirconium, gallium and indium, and B represents the valence of the above mentioned metal.

Examples of such iodine compounds are iodine $I_2$, hydrogen iodide HI, chlorine iodide ICl, butyl iodide $C_4H_5I$, amyl iodide $C_5H_{11}I$,

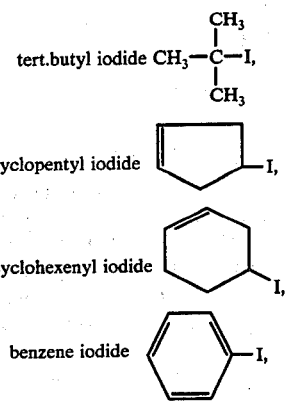

tetramethylene diiodide I—$CH_2)_4I$, iodoform H—C—$I_3$, allyl iodide $CH_2=CH-CH_2-I$, 1,4-diiodo-2-butene I—$CH_2$—CH = CH — $CH_2$—I, 1,4-diiodo-2-methyl-2-butene

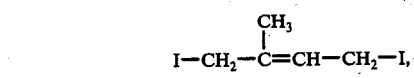

1,4-diiodo-2,3-dimethyl-2-butene

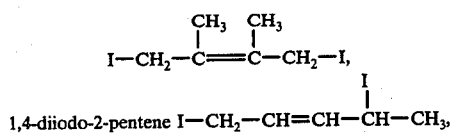

1,4-diiodo-2-pentene I—$CH_2$—CH=CH—CH—$CH_3$, aluminum iodide $AlI_3$, titanium iodide $TiI_4$, zinc iodide $ZnI_2$, zirconium iodide $ZrI_4$, gallium iodide $GaI_3$, tin iodide $SnI_4$, indium iodide $InI_3$, sodium iodide NaI, and lithium iodide LiI. These iodine compounds may be used as a mixture of two or more of the above mentioned compounds.

In the case where the zirconium compound containing a zirconium atom and an iodine atom in one molecule as in di(butoxy)-diiodozirconium and tri(ethoxy)-monoiodozirconium is used as the zirconium compound component, the iodine compound component need not be newly added and may be omitted.

3. Organoaluminum compound

In general, organoaluminum compounds which can be used in combination with the transition metal component of Ziegler catalysts can be used in the process of this invention.

Particularly preferred organoaluminum compounds are those which are represented by the formula $AlR''_mCl_{3-m}$ wherein $R''$ represents an alkyl group having from 1 to 10 carbon atoms, preferably from 1 to 6 carbon atoms, a cycloalkyl group having from 3 to 10 carbon atoms, preferably 3 to 6 carbon atoms or an aryl group having from 6 to 10 carbon atoms such as pheny, tolyl or xylyl; and m is 1.5 or 2.

Examples of such organoaluminum compounds are dimethylaluminum chloride, diethylaluminum chloride, diisobutylaluminum chloride, diphenylaluminum chloride, diethylaluminum iodide, methylaluminum sesquichloride, ethylaluminum sesquichloride, and butylaluminum sesquichloride. These organoaluminum compounds can be used as a mixture of two or more thereof.

4. Catalyst composition

The components I, II and III are preferably used in a ratio within the range described below. If these quantative balances are disturbed or destroyed, the catalytic performance of the resulting catalyst will tend to deteriorate.

1. The quantity of the zirconium compound (Zr) used may vary within a wide range. In general, the zirconium compound is preferably used in the molar ratio of Zr to IP (isoprene feed) (Zr/IP) of 0.00005 to 0.01, more preferably 0.0001 to 0.001.

2. The iodine compound (I) is used in a molar ratio of I to Zr (I/Zr) of 0.5 to 5, preferably 1 to 3.

3. The organoaluminum compound (Al) is used in a molar ratio of Al to Zr (Al/Zr) of 1 to 100, preferably 3 to 30.

5. Catalyst preparation

The catalyst system which can be used in the present invention can be prepared by mixing the respective components as stated above in an atmosphere of an inert gas.

When the respective components are mixed together, it is preferable that the zirconium compound and the iodine compound be added in order to a solvent and, after mixing, the aluminum compound be added to the mixture. A solvent usable for the catalyst preparation is preferably selected from those solvents which are used in the catalytic dimerization process as described hereinafter.

The catalyst preparation is suitably carried out at a temperature within the range of 30 to 80° C. As stated before, a coordinating compound such as a phosphine, a phosphite, a sulfoxide, an amine, a nitrile and an aldehyde may be further added to the catalyst system in order to facilitate the solubilization of the catalyst or to suppress the formation of an oligomer (a highly viscous product). However, the catalyst system of the present invention does not necessarily require the addition of these coordinating compounds.

2. Catalytic dimerization

While, in the catalytic dimerization of the present invention, an aromatic hydrocarbon such as benzene, toluene, or xylene or an aliphatic hydrocarbon such as hexane or heptane may be used as a solvent, the aromatic hydrocarbons suitable for solubilizing the catalyst are preferred.

The catalytic dimerization is carried out at a temperature of 0° to 200° C, preferably 50° to 120° C.

A fraction of 2,6-dimethyl-1,3,6-octatadiene (DMOT) having a boiling point of 50° to 60° C was obtained under a reduced pressure of 10 to 15 mmHg. The quantity and yield are shown in Table 1.

Table 1

| Example NO. | Zirconium compound (millimole) | Iodine compound (millimole) | Additive (millimole) | Reaction temperature (° C) | DMOT quantity g | DMOT yield % |
|---|---|---|---|---|---|---|
| 1 | zirconium tetraoctanoate 0.3 | allyl iodide 0.6 | triphenyl-phosphine 0.2 | 120 | 85.6 | 84 |
| 2 | tetrachloro-propoxy-zirconium 0.25 | iodine 0.5 | — | 110 | 83.6 | 82 |
| 3 | zirconyl diacetate 0.45 | allyl iodide 0.8 | tricresyl phosphate 0.45 | 120 | 80.6 | 79 |
| 4 | tributoxy-chloro-zirconium 0.6 | 1,4-diiodo butene 0.6 | — | 130 | 81.5 | 80 |
| 5 | zirconium tetranaphthe-nate 0.75 | butyl iodide 0.75 | tributyl-phosphine 0.2 | 120 | 84.7 | 83 |
| 6 | diphenoxydich-loro-zirconium 0.4 | alunimum iodide 0.8 | — | 100 | 82.6 | 81 |
| 7 | tetrabutoxy-zirconium 0.5 | tetraiodo-titanium 0.3 | dimethyl sulfoxide 0.2 | 80 | 77.5 | 76 |
| 8 | tetrachloro-propoxy-zirconium 0.25 | iodine 0.5 | triphenyl phosphine 0.25 | 110 | 81 | 79 |

The catalytic dimerization can be carried out under normal pressure and under increased pressures.

The other reaction conditions, reaction procedures, catalyst decomposition and removal and recovery of the desired products are set or adopted according to the conventional practice.

Several illustrative and non-limitative examples follow:

EXAMPLES 1 THROUGH 7

In each of Examples 1 through 7, a 500-ml. autoclave was flushed with a nitrogen gas to displace the air contained therein with the nitrogen gas. Then, 150 ml. of toluene, the iodine compound, the zirconium compound and, according to necessity, the additives which are indicated in Table 1 were placed in the autoclave and these compounds were stirred at a temperature of 40° C for 1 hour.

Then, 5 millimoles of diethylaluminum chloride and 102g of isoprene (1.5 moles) were introduced into the autoclave and the mixture was stirred at a pre-determined temperature for 5 hours.

Thereafter, methanol was added to the reaction mixture to decompose the catalyst and the reaction mixture was distilled to separate the reaction products therefrom.

EXAMPLE 9

The effect of the iodine compound addition on the catalytic dimerization of isoprene was examined by changing the molar ratio of zirconium compound to isoprene (Zr/IP). In the carrying out of the catalytic dimerization, the catalyst and the reaction conditions were similar to those of Example 1 except that the molar ratio of Zr/IP and the addition quantity of the iodine compound were varied. The results are shown in Table 2.

It is apparent from Table 2 that the catalyst with the iodine compound added thereto according to the present invention is useful even if the molar ratio of Zr/IP is much lower than a range of 0.002 to 0.02 which is deemed to be suitable in the prior art (see, Japanese Patent Laid Open Publication NO. 5706/73).

Table 2

| | | Effect of iodine compound addition | | | |
|---|---|---|---|---|---|
| Molar ratio of zirconium compound to isoprene Zr/IP | Molar ratio of iodine compound to zirconium I/Zr | Percent conversion of isoprene (%) | Percent selectivity to DMOT (%) | Percent yield of DMOT (%) | Yield on catalyst basis DMOT/Zr compd. (g/g) |
| 0.0002 (Example 1) | 2 | 94 | 89.3 | 84 | 430 |
| 0.0002 | 0.5 | 71 | 78.5 | 56 | 287 |
| 0.0002 | 0 | 37 | 67.0 | 25 | 128 |
| 0.002 | 2 | 98 | 87.7 | 86 | 44 |
| 0.002 | 0 | 46 | 72.0 | 33 | 17 |

We claim:

1. A process for producing 2,6-dimethyl-1,3,6-octatriene which comprises contacting isoprene with a dimerization catalyst thereby to dimerize the isoprene, said dimerization catalyst comprising a combination of:
   I. a zirconium compound selected from the group consisting of:
      1. compounds having the general formula $ZrX_{4-n}Y_n,$ 2. compounds having the general formula $ZrOY'_2,$ and 3. complexes of the compound (1) or (2) with a coordinating compound, wherein X represents a halogen atom; Y and Y' respectively represent a member selected from the group consisting of (i) alkoxy and chloroalkoxy groups each having from 1 to 20 carbon atoms, (ii) aryloxy and chloroaryloxy groups wherein each aryloxy group is a member selected from the group consisting of phenoxy and methyl-substituted phenoxy groups, and (iii) acyloxy groups each having the general formula RCOO-wherein R is a member selected from the group consisting of alkyl groups each having from 1 to 20 carbon atoms and aryl groups each having from 6 to 20 carbon atoms; and n is an integer of 1 to 4:

II. an iodine compound which is a member selected from the group consisting of those having either of the general formulas $R'I_A$ and $MeI_B$ wherein R' represents a member selected from the group consisting of hydrogen, halogen atoms, straight and branched chain hydrocarbon groups each having from 1 to 20 carbon atoms and cyclic hydrocarbon groups each having from 3 to 10 carbon atoms; A is an integer of 1 to 3; Me represents a metal of Groups I through IV of the periodic table; and B represents the valence of the metal; and III. an organoaluminum compound having the general formula.

$AlR''_m Cl_{3-M}$ wherein R'' represents a member selected from the group consisting of alkyl groups each having from 1 to 10 carbon atoms, cyclic alkyl groups each having from 3 to 10 carbon atoms, and aryl groups each having 6 to 10 carbon atoms; and m is 1.5 or 2; in which dimerization catalyst, when iodine is present as a ligand in the zirconium compound I, the iodine compound II may be excluded.

2. The process as claimed in claim 1 in which the zirconium compound is the compound (1) and is selected from the group consisting of zirconium tetraoctanoate, tetrachloropropoxy zirconium, tributoxychlorozirconium, zirconium tetranaphthenate, diphenoxydichlorozirconium, and tetrabutoxy zirconium.

3. The process as claimed in claim 1 in which the zirconium compound is the compound (2) and is selected from the group consisting of zirconyl diacetate, zirconyl dioctanoate, zirconyl dihexanoate, and zirconyl dinaphthenate.

4. The process as claimed in claim 1 in which the zirconium compound is the complex (3) wherein the coordinating compound is selected from the group consisting of ethers, amines, sulfoxides, sulfones, sulfolanes and phosphines.

5. The process as claimed in claim 4 in which the phosphine is selected from the group consisting of tributyl phosphine, tricresyl phosphine and triphenyl phosphine.

6. The process as claimed in claim 4 in which the sulfoxide is dimethylsulfoxide.

7. The process as claimed in claim 4 in which the complex (3) is produced in situ in the dimerization from the compound (1) or (2) and the coordinating compound.

8. The process as claimed in claim 1 in which the iodine compound is selected from the group consisting of iodine, allyl iodide, 1,4-diiodobutene, butyl iodide, aluminum iodide, and tetraiodotitanium.

9. The process as claimed in claim 1 in which the molar ratio of the iodine compound to the zirconium compound is from 0.5 to 5, and the molar ratio of the organoaluminum compound to the zirconium compound is from 1 to 100.

10. The process as claimed in claim 1 in which the molar ratio of the zirconium compound to the isoprene is from 0.00005 to 0.01.

11. The process as claimed in claim 1 in which the isoprene is contacted with the dimerization catalyst at a temperature from 0° to 200° C.

12. The process as claimed in claim 1 in which the isoprene is contacted with the catalyst in a hydrocarbon solvent.

* * * * *